US00PP34933P2

(12) United States Plant Patent
Conner

(10) Patent No.: US PP34,933 P2
(45) Date of Patent: Jan. 24, 2023

(54) PECAN TREE NAMED 'GA. 03-6-32'

(50) Latin Name: *Carya illinoinensis*
Varietal Denomination: Ga. 03-6-32

(71) Applicant: University of Georgia Research Foundation, Inc., Athens, GA (US)

(72) Inventor: Patrick Conner, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/686,919

(22) Filed: Mar. 4, 2022

(51) Int. Cl.
*A01H 5/00* (2018.01)

(52) U.S. Cl.
USPC ..... Plt./153

(58) Field of Classification Search
USPC ..... Plt./153
See application file for complete search history.

*Primary Examiner* — Annette H Para
(74) *Attorney, Agent, or Firm* — Thomas Horstemeyer, LLP

(57) ABSTRACT

A pecan tree distinguished by the following unique combination of characteristics: large nut size, bright kernel color, good shelling ability, moderately early harvest date, and good resistance to the scab fungus (*Venturia effuse*) in sprayed orchards.

5 Drawing Sheets

Botanical designation: *Carya illinoinensis*.
Cultivar denomination: 'Ga. 03-6-32'.

BACKGROUND OF THE INVENTION

The present invention relates to a new and distinct cultivar of *Carya*, botanically know as *Carya illinoinensis*, and hereinafter referred to by the cultivar name 'Ga. 03-6-32'.

The new *Carya illinoinensis* 'Ga. 03-6-32' is a product of a planned breeding program conducted by the inventor in Tifton, Ga. In 2003 the cross 03-6 ('Sioux' x 'Desirable') was made by Patrick Conner at a horticulture farm in Tifton, Ga. 'Sioux' (unpatented) is a 1962 USDA release which is notable for its light kernel color, excellent shelling ability, and vigorous growth. 'Sioux' was at one time recommended for planting in Georgia, but large plantings were not made because nut size is too small (6.2 g) to bring maximum prices. 'Desirable' (unpatented) was the most planted pecan cultivar in Georgia for several decades. Attractive traits of 'Desirable' are large nut size, consistent bearing, light kernel color, and excellent shelling ability into complete halves. Unfortunately, 'Desirable' has become extremely susceptible to pecan scab disease, caused by the fungus *Venturia effuse*, and is therefore no longer recommended for planting in southern Georgia where scab is more prevalent. Cross 03-6 produced 205 nuts, from which 124 seedlings were transplanted into a seedling orchard after growing the seedlings in pots for one year and removing those with symptoms of pecan scab on the foliage. Seedlings were transplanted into the seedling orchard in 2005 on the Tifton Campus. 'Ga 03-6-32' first fruited in 2008, when it was selected for its large size (10.2 g) and high percent kernel (60%). 'Ga. 03-6-32' was selected for yield trials in 2009.

Asexual reproduction of 'Ga. 03-6-32' was performed by grafting (top working) onto 'Newt' (unpatented) pecan trees in 2009 at Tifton, Ga., and whip grafting pecan seedlings at Ray City, Ga., and Albany, Ga. was performed in order to evaluate these trees. Continued asexual reproduction of 'Ga. 03-6-32' has shown that the unique features of the new 'Ga. 03-6-32' reproduced true to form, are firmly fixed, and are established and transmitted through succeeding propagations.

BRIEF SUMMARY OF THE INVENTION

The new pecan tree 'Ga.03-6-32' has not been observed under all possible environmental conditions. Certain phenotypical characteristics of this variety, such as growth and color, may vary with changing environmental conditions and cultural practices such as temperature, water and fertility levels, soil types, nutrient availability and light intensity without, however, any variance in genotype.

'Ga.03-6-32' is distinguished from other pecan varieties known to the inventor due to the following unique combination of characteristics: large nut size, bright kernel color, good shelling ability, moderately early harvest date, and good resistance to the scab fungus in sprayed orchards. These traits have been repeatedly observed and are determined to be the unique and distinguishing characteristics of the new *Carya illinoinensis* 'Ga. 03-6-32'. Pecan trees of the new 'Ga.03-6-32' differ from the parent 'Sioux' at least by having larger average nut size and differ from parent 'Desirable' at least by better resistance to pecan scab disease. Differences from other pecan cultivars are presented in the tables below.

BRIEF DESCRIPTION OF THE DRAWINGS

The accompanying colored photographic illustrations show the overall appearance and distinct characteristics of the new cultivar of *Carya illinoinensis* 'Ga. 03-6-32' showing the colors as true as possible. Colors in the photographs may differ slightly from the color values cited in the detailed botanical description, which accurately describes the colors of the new Genus species 'cultivar name'. The data in FIG. 1 was based on data collected from four grafted trees on their first through eleventh year from top-working grafts.

FIG. 2 is a photograph showing the form and color of the stigma of 'Ga. 03-6-32'.

FIG. 3 is a photograph showing the nut and kernel of 'Ga. 03-6-32' nuts.

FIG. 4 is a photograph showing nut shape and kernel characteristics of 'Ga. 03-6-32' (center) in comparison to parent cultivars 'Desirable' (top) and 'Stuart' (bottom).

DETAILED DESCRIPTION

Botanical:

The following detailed description of 'Ga. 03-6-32' is based on observations of the original tree growing in Tifton, Ga. at ages 15 and 16 and of asexually reproduced progeny on their first through eleventh years from top-working grafts, growing in Tifton, Ga., and whip grafted trees on their first through eighth year in Ray City and Albany, Ga.

Throughout this specification, color names beginning with a small letter signify that the name of that color, as used in common speech, is aptly descriptive. Color names beginning with a capital letter designate values based made with reference to The Royal Horticultural Society (R.H.S.) Colour Chart, 2005. The color characteristics of this type may vary with lighting and other conditions. Therefore, color characteristics of this new variety should be determined with reference to the observations described herein, rather than from these illustrations alone.

Varietal Name: 'Ga. 03-6-32'.

Parentage: Seed parent: 'Sioux'; Pollen parent: 'Desirable'.

Figure 5:
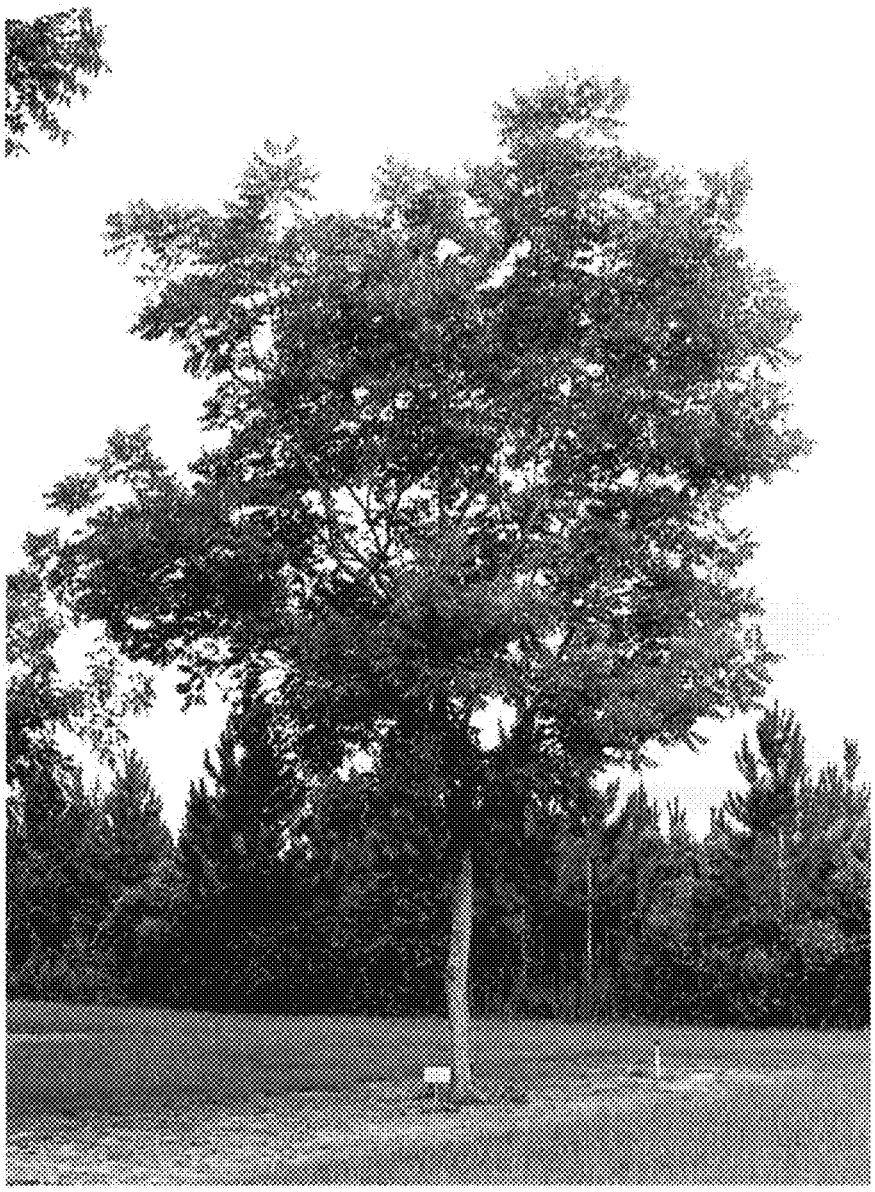
FIG. 5 is a photograph showing the form of an 11-year-old tree of 'Ga. 03-6-32' grown in Tifton, Ga.

Description of plant material:

*Tree*.—'Ga. 03-6-32' trees are vigorous with an upright moderately spreading canopy. Trunks have tight scales greyed green in color (RHS N200C). The 'Ga. 03-6-32' trees have a dense branching pattern. In 2018 the height of the original, 15-year-old 'Ga. 03-6-32' tree was about 14 meters in height and had a canopy width of about 10.7 meters. In 2022, the heigh of an 11-year-old 'Ga. 03-6-32' tree, shown in FIG. 5, was about 9.9 meters in height with a canopy width of about 7.7 meters.

*Leaf*.—The mature leaf is odd pinnate compound. Leaves are dark green (RHS 137A) on the adaxial side and lighter in color on the abaxial side (RHS 147B). Each mature leaf has about 11 to 15 leaflets. Size of mature leaves (fourth leaf from the base of shoot) is about 40 to 52 cm long and about 30 to 35 cm wide. Leaflets are falcate in shape. Fourth leaflet on the fourth leaf is about 3 to 4 cm wide and about 14 to 16 cm long. The petiole on the fourth leaflet of the fourth leaf is about 3 mm long and 1.5 mm wide and yellow green (RHS 144B) in color. Leaf (bud) burst is late, averaging around April 3 in Tifton Ga. as shown in Table 8. Time of leaf fall is late Autumn, typically around December 2, but very dependent upon yearly weather.

Figure 1:
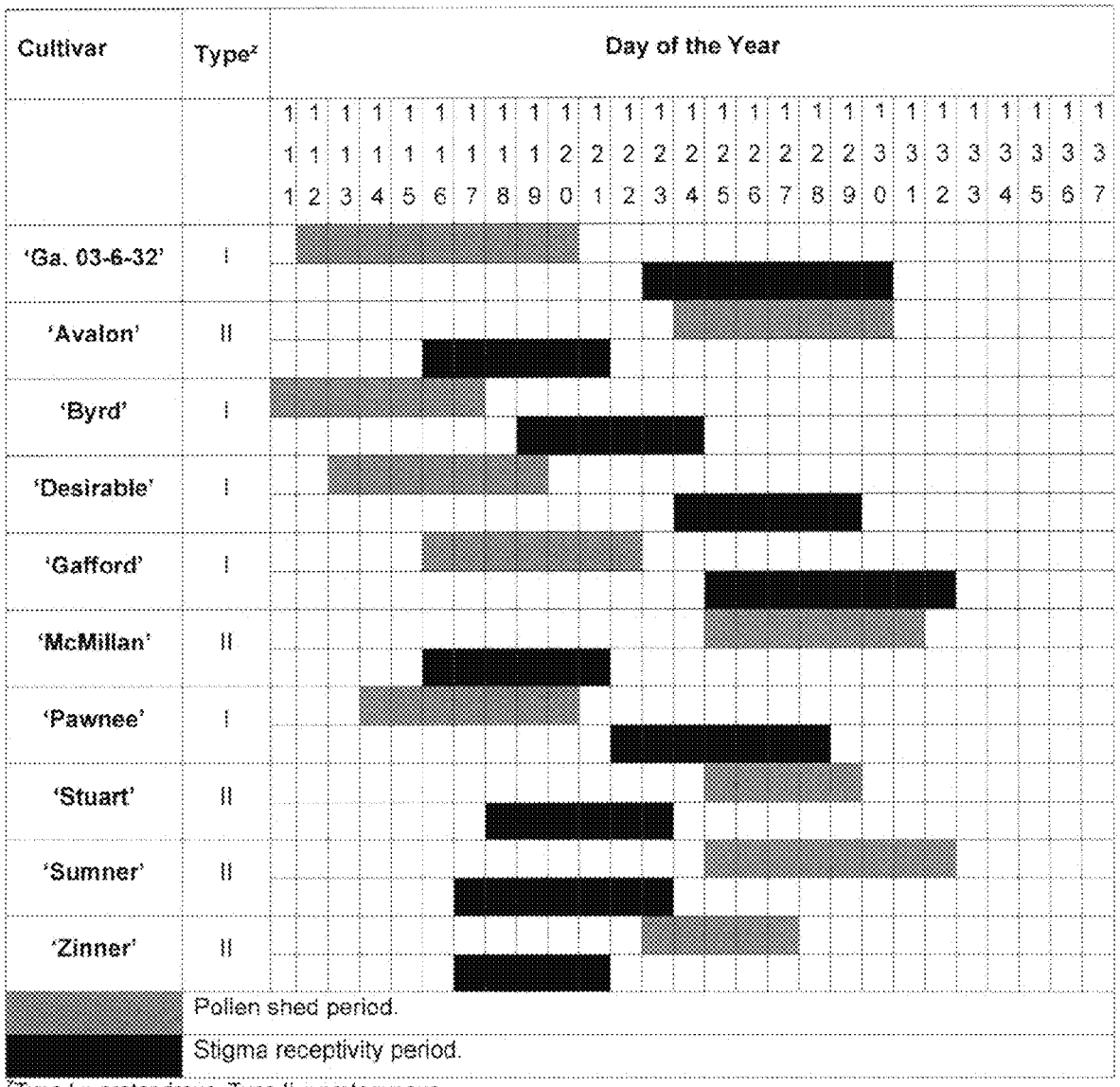
FIG. 1 is a pollination chart showing the timing of pollen shed and stigma receptivity of 'Ga. 03-6-32' in comparison to several other pecan cultivars grown in Tifton, Ga.
Figure 2:
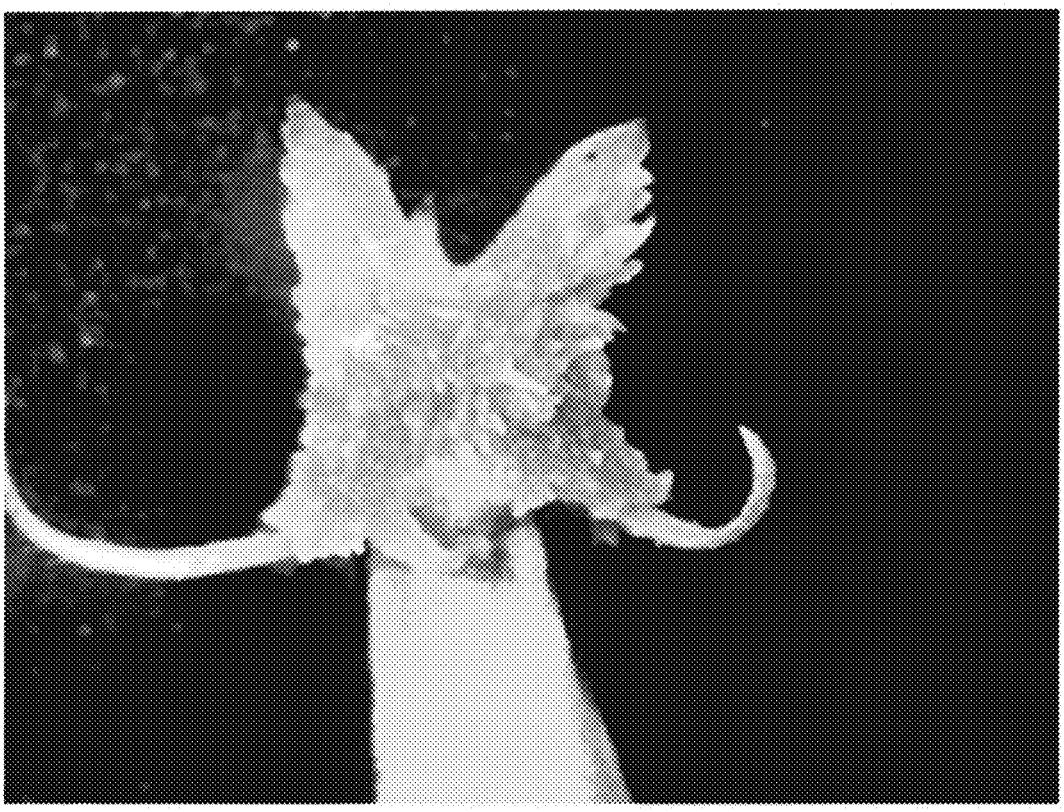
FIGS. 2, 3 and 4 are from the 15-year-old original tree in Tifton, Ga.

*Flower*.—'Ga. 03-6-32' is protandrous in flowering (type I) with early season pollen shed and mid to late season receptivity (FIG. 1). It would be pollinated by 'Avalon' (U.S. Plant Pat. No. 30,227), 'McMillan' (unpatented), 'Stuart' (unpatented), 'Sumner' (unpatented), and 'Zinner' (unpatented). It would pollinate these same cultivars. The stigma is medium in size, upright with moderately large lobes, and yellow green (RHS 154A) with an orange-red blush (RHS 31B) in color (FIG. 2). The stigma is typically about 4.8 mm long and about 2.5 mm wide. The stigma is moderately splitting. Pigment of the stigma is present, but very light with weak anthocyanin. Determinate pendulous catkin. Typical length of catkin is about 92 mm and typical width is about 4 mm.

*Nut in shuck*.—Topography is smooth and shuck texture is papery. Shuck suture wings are prominent (about 2-3 mm in height). Shuck color is moderately bright yellow green (RHS 144A). Shuck apex is obtuse. Shucks are not persistent after nut fall. Typical time of 50% shuck opening is around October 4 in Tifton, Ga. as given in Table 8. No striping or ribs are present on the nut shuck.

Figure 3:
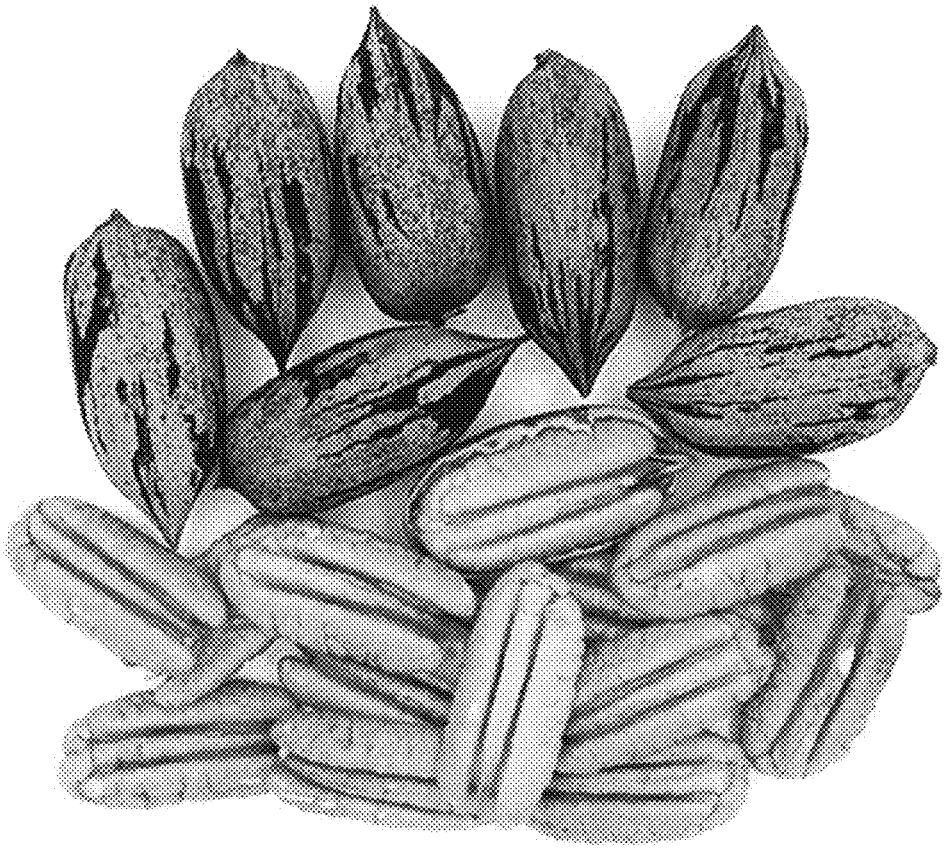

*Dry nut*.—Nut shells have prominent shell striping which extends from the apex to the base (FIG. 3). Dots are small (about 0.5 to 2.5 mm diameter), numerous, present from base to apex, and dark brown in color (RHS200A). Nut shape is oblong with a cuspidate to mucronate base and an acuminate, grooved apex. Nuts are round in cross section. Shell topography is slightly bumpy with ridges from the base to the apex. Shell thickness is medium and about 0.8-0.9 mm thick at the equator. Nuts of 'Ga. 03-6-32' average about 55 mm in length, about 24 mm in width, with about a 10 mm tip. Nuts are greyed orange in color (RHS 177B). Kernel size of the nuts is large. Typical weight of the kernel is 5.8 g.

Figure 4:
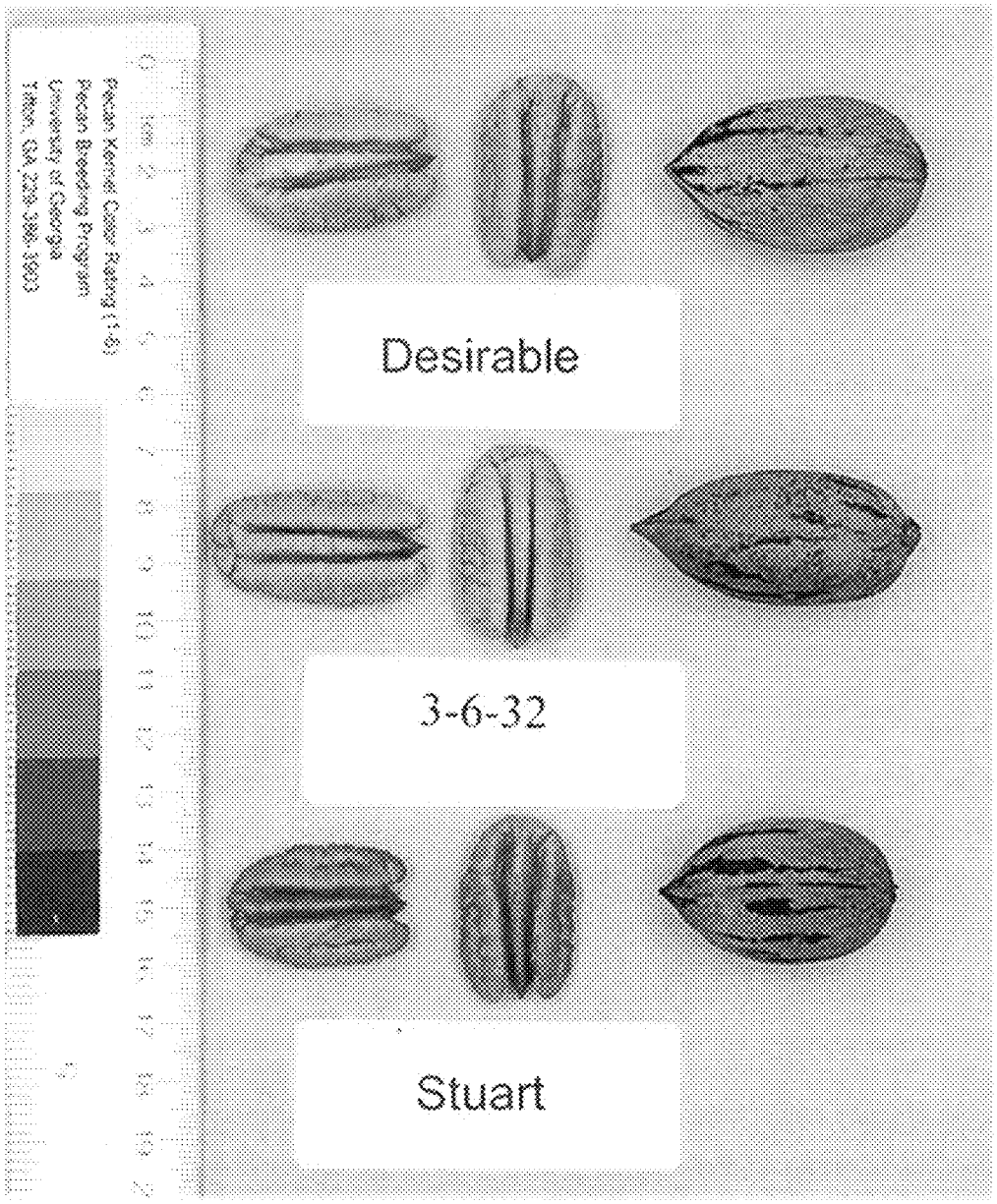

Comparisons to other varieties:

*Comparison to parents*.—In comparison to 'Sioux', 'Ga. 03-6-32' has a larger nut. 'Ga. 03-6-32' has a typical nut size of about 10.2 g, while 'Sioux' has a typical nut size of about 6.0 g. In comparison to 'Desirable', 'Ga. 03-6-32' has a higher percentage kernel. 'Desirable' nuts are normally composed of about 52% kernel while 'Ga. 03-6-32' nuts typically have about 56 to 57% kernel. 'Ga. 03-6-32' nuts are also a different shape from 'Desirable' nuts. 'Desirable' nuts have a round base and oval cross-section while 'Ga. 03-6-32' nuts have a cuspidate to mucronate base with a round cross sections (FIG. 4).

*Scab resistance*.—'Ga. 03-6-32' has shown moderate resistance to pecan scab in replicated tests. Trees were grown in a sprayed orchard at Tifton in 2012 to 2019, and leaf and nut scab symptoms were similar to or better than other cultivars tested (Table 1). In the Ray City sprayed yield trial in years 2017 to 2019, no scab symptoms were recorded (Table 2). In an unsprayed trial in Tifton, Ga. from 2013 to 2019, Ga. 03-6-32 had mild leaf scab and moderate nut scab damage (Table 1). In an Albany, Ga. unsprayed trial, Ga. 03-6-32 also had moderate leaf and nut scab damage. Overall, in sprayed trial Ga. 03-6-32 has little or no scab infection, whereas in unsprayed trials Ga. 03-6-32 rates better than susceptible cultivars like 'Desirable' and 'Pawnee' (unpatented) and worse than strongly resistant cultivars like 'Avalon' and 'Elliott' (unpatented).

*Production*.—To evaluate yield, 'Ga. 03-6-32' was topworked into a bearing orchard at Tifton, Ga.

Using this method, 'Ga. 03-6-32' appears to be a good yielding tree with yields steadily increasing each year, except for year six (Table 5). Yields of whip-grafted trees at Ray City were less than the high yielding 'Avalon', similar to 'Zinner' and higher than the industry standard, 'Desirable' (Table 6). Cluster size of 'Ga. 03-6-32' is 2.4, which is similar to other cultivars with stable bearing habits ('Desirable', 'Stuart', and 'Zinner') and less than alternating cultivars that need crop thinning ('Byrd', 'McMillan', 'Pawnee', and 'Sumner'). Moderate cluster size and relatively stable yields indicate that 'Ga. 03-6-32' will have a reduced need for crop thinning.

*Nut quality*.—Nut size (10.2 g) and percent kernel (56.7%) (Table 7) fall within the range needed for optimum prices in the current market. Shellers generally want nut size to be larger than 9 g and more than 52% kernel for shipping to the Chinese market. 'Ga. 03-6-32' has similar size to 'Desirable' and a higher percent kernel (Table 7). Additionally, 'Ga. 03-6-32' has little incidence of packing material sticking to the kernel and highly attractive kernels (Table 7).

*Adaptation*.—'Ga. 03-6-32' is late to break bud in the spring (Table 8) which indicates some measure of frost avoidance if planted in the northern part of Georgia. For many years 'Stuart' was recommended for north Georgia, and budbreak of 'Ga. 03-6-32' is similar to 'Stuart'. Harvest date is almost a week ahead of 'Desirable' (Table 8) which puts it in the early mid-season harvest period. This would make 'Ga. 03-6-32' among the first cultivars to be harvested, but not so early that extra protection from predators like crows would be necessary. 'Ga. 03-6-32' has low susceptibility to black pecan aphid (*Melanocallis caryaefoliae*) (Tables 1, 2, 3, 4).

TABLE 1

Pest resistance of pecan cultivars and selections in a sprayed orchard over years 2012-2019 at Tifton, Ga.

| Cultivar | # Trees | Leaf scab[z] | Avg. nut scab[y] | Max. nut scab[x] | Black aphid damage[w] |
|---|---|---|---|---|---|
| 'Ga. 03-6-32' | 4 | 1.3 b[v] | 1.0 d | 1.4 d | 1.1 de |
| 'Avalon' | 6 | 1.0 b | 1.0 d | 1.0 d | 2.1 b |
| 'Byrd' | 5 | 1.1 b | 2.1 b | 3.5 b | 1.2 cde |
| 'Desirable' | 6 | 2.9 a | 3.7 a | 4.8 a | 1.4 cd |
| 'Gafford' | 4 | 1.0 b | 1.0 d | 1.0 d | 1.0 e |
| 'Pawnee' | 3 | 1.1 b | 1.4 cd | 2.6 c | 1.5 c |
| 'Stuart'[u] | 5 | 1.1 b | 1.4 c | 3.1 bc | 2.5 a |
| 'Zinner'[u] | 6 | 1.1 b | 1.1 d | 2.7c | 2.6 a |
| Sig. | | <0.001 | <0.001 | <0.001 | <0.001 |

[z]1 = no scab lesions, 2 = a few isolated lesions with restricted growth, 3 = multiple lesions with expanding lesions, 4 = stem scab lesions or defoliation.
[y]1 = no scab lesions, 2 = a few lesions with restricted growth, 3 = multiple lesions, 0% to 10% coverage, 4 = 11% to 50% coverage, 5 = 51% to 100% coverage or nut drop. Average damage seen on nuts over the tree.
[x]1 = no scab lesions, 2 = a few lesions with restricted growth, 3 = multiple lesions, 0% to 10% coverage, 4 = 11% to 50% coverage, 5 = 51% to 100% coverage or nut drop. Maximum damage seen on any nut.
[w]1 = no damage, 2 = light chlorotic spotting, 0% to 25% leaves affected, 3 = moderate chlorotic spotting, 26% to 75% chlorotic spotting, 4 = heavy chlorotic spotting, 76% to 100% leaves affected.
[v]Mean separation within a column by Duncan's multiple range test, P ≤ 0.05.
[u]Trees were removed after hurricane in 2018 and have no data for 2019.

TABLE 2

Pest resistance of pecan cultivars and selections in a sprayed orchard over years 2017-2019 at Ray City, Ga.

| Cultivar | # Trees | Leaf scab[z] | Avg. nut scab[y] | Max. nut scab[x] | Black aphid damage[w] |
|---|---|---|---|---|---|
| 'Ga. 03-6-32' | 6 | 1.0 b[v] | 1.0 b | 1.0 c | 1.0 b |
| 'Avalon' | 6 | 1.0 b | 1.0 b | 1.0 c | 1.9 a |
| 'Desirable' | 6 | 1.8 a | 2.7 a | 3.4 a | 1.0 b |
| 'Elliott' | 6 | 1.0 b | 1.0 b | 1.0 c | 1.0 b |
| 'Zinner' | 6 | 1.0 b | 1.4 b | 2.1 b | 1.6 a |
| Sig. | | <0.001 | <0.001 | <0.001 | <0.001 |

[z]1 = no scab lesions, 2 = a few isolated lesions with restricted growth, 3 = multiple lesions with expanding lesions, 4 = stem scab lesions or defoliation.
[y]1 = no scab lesions, 2 = a few lesions with restricted growth, 3 = multiple lesions, 0% to 10% coverage, 4 = 11% to 50% coverage, 5 = 51% to 100% coverage or nut drop. Average damage seen on nuts over the tree.
[x]1 = no scab lesions, 2 = a few lesions with restricted growth, 3 = multiple lesions, 0% to 10% coverage, 4 = 11% to 50% coverage, 5 = 51% to 100% coverage or nut drop. Maximum damage seen on any nut.
[w]1 = no damage, 2 = light chlorotic spotting, 0% to 25% leaves affected, 3 = moderate chlorotic spotting, 26% to 75% chlorotic spotting, 4 = heavy chlorotic spotting, 76% to 100% leaves affected.
[v]Mean separation within a column by Duncan's multiple range test, P ≤ 0.05.

TABLE 3

Pest resistance of pecan cultivars and selections in an unsprayed orchard over years 2013-2019 at Tifton, Ga.

| Cultivar | # Trees | Leaf scab[z] | Avg. nut scab[y] | Max. nut scab[x] | Black aphid damage[w] |
|---|---|---|---|---|---|
| 'Ga. 03-6-32' | 2 | 1.9 c[v] | 2.9 c | 3.8 b | 1.5 d |
| 'Avalon' | 3 | 1.0 c | 1.0 e | 1.2 c | 2.4 abc |
| 'Cunard' | 1 | 3.2 ab | 4.8 ab | 5.0 a | 1.8 bcd |
| 'Desirable' | 1 | 3.9 a | 5.0 a | 5.0 a | 2.1 bcd |
| 'Elliott' | 1 | 1.0 c | 1.0 e | 1.0 c | 1.6 cd |
| 'McMillan' | 1 | 1.0 c | 1.0 e | 1.2 c | 1.7 cd |
| 'Pawnee' | 1 | 2.1 bc | 4.8 ab | 4.9 a | 2.0 bcd |
| 'Stuart' | 1 | 2.1 bc | 4.6 ab | 5.0 a | 3.1 a |
| 'Sumner' | 1 | 1.6 c | 2.4 d | 3.4 b | 2.1 bcd |
| 'Zinner' | 2 | 1.9 c | 4.4 b | 4.9 a | 2.7 ab |
| Sig. | | <0.001 | <0.001 | <0.001 | <0.001 |

[z]1 = no scab lesions, 2 = a few isolated lesions with restricted growth, 3 = multiple lesions with expanding lesions, 4 = stem scab lesions or defoliation.
[y]1 = no scab lesions, 2 = a few lesions with restricted growth, 3 = multiple lesions, 0% to 10% coverage, 4 = 11% to 50% coverage, 5 = 51% to 100% coverage or nut drop. Average damage seen on nuts over the tree.
[x]1 = no scab lesions, 2 = a few lesions with restricted growth, 3 = multiple lesions, 0% to 10% coverage, 4 = 11% to 50% coverage, 5 = 51% to 100% coverage or nut drop. Maximum damage seen on any nut.
[w]1 = no damage, 2 = light chlorotic spotting, 0% to 25% leaves affected, 3 = moderate chlorotic spotting, 26% to 75% chlorotic spotting, 4 = heavy chlorotic spotting, 76% to 100% leaves affected.
[v]Mean separation within a column by Duncan's multiple range test, P ≤ 0.05. Years were treated as reps.

TABLE 4

Pest resistance of pecan cultivars and selections in an unsprayed orchard over years 2016-2019 at Albany, Ga.

| Cultivar | # Trees | Leaf scab[z] | Avg. nut scab[y] | Max. nut scab[x] | Black aphid damage[w] |
|---|---|---|---|---|---|
| 'Ga. 3-6-32' | 3 | 1.4 b[v] | 2.2 b | 3.8 b | 1.9 |
| 'Avalon' | 3 | 1.0 c | 1.0 c | 1.0 c | 2.5 |
| 'Cunard' | 2 | 4.0 a | 5.0 a | 5.0 a | 2.0 |
| 'Desirable' | 3 | 3.9 a | 5.0 a | 5.0 a | 2.0 |
| 'Elliott' | 3 | 1.0 c | 1.0 c | 1.0 c | 2.3 |
| 'Sumner' | 3 | 1.0 c | 2.0 bc | 3.9 b | 2.1 |

TABLE 4-continued

Pest resistance of pecan cultivars and selections in an unsprayed orchard over years 2016-2019 at Albany, Ga.

| Cultivar | # Trees | Leaf scab[z] | Avg. nut scab[y] | Max. nut scab[x] | Black aphid damage[w] |
|---|---|---|---|---|---|
| 'Treadwell' | 2 | 4.0 a | 5.0 a | 5.0 a | 1.6 |
| Sig. | | <0.001 | <0.001 | <0.001 | NS |

[z]1 = no scab lesions, 2 = a few isolated lesions with restricted growth, 3 = multiple lesions with expanding lesions, 4 = stem scab lesions or defoliation.

[y]1 = no scab lesions, 2 = a few lesions with restricted growth, 3 = multiple lesions, 0% to 10% coverage, 4 = 11% to 50% coverage, 5 = 51% to 100% coverage or nut drop. Average damage seen on nuts over the tree.

[x]1 = no scab lesions, 2 = a few lesions with restricted growth, 3 = multiple lesions, 0% to 10% coverage, 4 = 11% to 50% coverage, 5 = 51% to 100% coverage or nut drop. Maximum damage seen on any nut.

[w]1 = no damage, 2 = light chlorotic spotting, 0% to 25% leaves affected, 3 = moderate chlorotic spotting, 26% to 75% chlorotic spotting, 4 = heavy chlorotic spotting, 76% to 100% leaves affected.

[v]Mean separation within a column by Duncan's multiple range test, P ≤ 0.05.

TABLE 5

In-shell nut yield (lbs. per tree) of pecan cultivars in Tifton, Ga. for years 10-14 (2015-2019) from planting.

| Cultivar | # Trees | Year 10 | Year 11 | Year 12 | Year 13 | Year 14 | Avg. |
|---|---|---|---|---|---|---|---|
| 'Ga. 3-6-32'[z] | 4 | 72 b[y] | 48 | 76 | 85 ab | 98 ab | 76 ab |
| 'Avalon'[z] | 6 | 69 b | 85 | 75 | 111 a | 125 a | 93 a |
| 'Byrd' | 5 | 95 a | 60 | 53 | 69 b | 50 c | 66 bc |
| 'Desirable' | 4 | 37 c | 50 | 50 | 52 b | 40 c | 46 c |
| 'Gafford' | 4 | 63 b | 67 | 76 | 85 ab | —[x] | 73 abc |
| 'Pawnee' | 3 | 12 c | 83 | 70 | 54 b | 62 bc | 56 bc |
| Sig. | | <0.001 | NS | NS | 0.03 | 0.009 | 0.014 |

[z]Ga. 03-6-32 and Avalon were topworked into the orchard and when yields were similar to year 7 yields they were considered to be 7 years old.

[y]Mean separation within a column by Duncan's multiple range test, P ≤ 0.05.

[x]Gafford yields were lost in 2018 (year 14) because it could not be harvested ahead of hurricane damage.

TABLE 6

In-shell nut yield (lbs. per tree) of pecan cultivars in Ray City, Ga. for years 6-8 from planting (2017-2019).

| Cultivar | # Trees | Yield year 6 | Yield year 7 | Yield year 8 | Yield avg. |
|---|---|---|---|---|---|
| 'Ga. 03-6-32' | 4 | 28 a[z] | 26 b | 49 a | 34 b |
| 'Avalon' | 3 | 35 a | 57 a | 68 a | 53 a |
| 'Desirable' | 4 | 10 b | 9 c | 19 b | 13 c |

TABLE 6-continued

In-shell nut yield (lbs. per tree) of pecan cultivars in Ray City, Ga. for years 6-8 from planting (2017-2019).

| Cultivar | # Trees | Yield year 6 | Yield year 7 | Yield year 8 | Yield avg. |
|---|---|---|---|---|---|
| 'Zinner' | 4 | 13 b | 40 ab | 44 a | 32 b |
| Sig. | | <0.001 | <0.001 | 0.01 | 0.002 |

[z]Mean separation within a column by Duncan's multiple range test, P ≤ 0.05.

TABLE 7

Nut and kernel quality attributes of pecan cultivars averaged over all years of testing (2009-2019) at Tifton, Ga.

| Cultivar | # Trees | Nuts/lb | Percent kernel | Percent fuzz[z] | Kernel rating[y] |
|---|---|---|---|---|---|
| 'Ga. 03-6-32' | 4 | 44.4 d[x] | 56.7 a | 0 c | 4.9 a |
| 'Avalon' | 6 | 47.2 bc | 53.8 b | 0 c | 4.6 a |
| 'Byrd' | 5 | 49.8 a | 56.5 a | 1.5 b | 3.9 b |
| 'Desirable' | 4 | 45.3 cd | 48.4 d | 4.6 a | 3.0 c |
| 'Gafford' | 4 | 49.2 ab | 50.4 c | 3.5 a | 3.5 b |
| 'Pawnee' | 3 | 47.1 bc | 56.0 a | 0 c | 3.8 b |
| Sig. | | <0.001 | <0.001 | <0.001 | <0.001 |

[z]Estimated percentage of the kernel surface covered with packing material.

[y]Attractiveness rating of the pecan kernels with 5 = Excellent, 4 = Good, 3 = Average, 2 = Poor, 1 = Terrible. Ratings are based on kernel color, size, fill, shelling ability, and lack of defects.

[x]Mean separation within a column by Duncan's multiple range test, P ≤ 0.05.

TABLE 8

Phenology & number of nuts/cluster of pecan cultivars in Tifton, Ga., 2011-2015.

| Cultivar | # Trees | Bud burst date | # Nuts per cluster | 50% Shuck split |
|---|---|---|---|---|
| 'Ga. 03-6-32' | 4 | 3-Apr ab[z] | 2.4 b | 4-Oct b |
| 'Avalon' | 6 | 4-Apr ab | 2.4 b | 2-Oct b |
| 'Byrd' | 5 | 25-Mar c | 3.2 a | 19-Sep c |
| 'Desirable' | 4 | 31-Mar b | 2.3 b | 10-Oct a |
| 'Stuart' | 5 | 3-Apr a | 2.6 b | 11-Oct a |
| 'Pawnee' | 3 | 31-Mar b | 3.4 a | 10-Sep d |
| Sig. | | <0.001 | <0.001 | <0.001 |

[z]Mean separation within a column by Duncan's multiple range test, P ≤ 0.05.

The 'Ga. 03-6-32' pecan tree is therefore an improved new and distinct pecan.

I claim:

1. A new and distinct cultivar of pecan tree of *Carya illinoinensis* named 'Ga. 03-6-32' substantially as herein illustrated and described.

* * * * *

[z]Type I = protandrous, Type II = protogynous